US 7,927,289 B2

(12) United States Patent
Cho et al.

(10) Patent No.: US 7,927,289 B2
(45) Date of Patent: Apr. 19, 2011

(54) CATHETER CAPABLE OF BEING EQUIPPED WITH MICRO BIOPSY TOOL

(75) Inventors: Dong-il Cho, Seoul (KR); Sun Kil Park, Bucheon-si (KR); Ah Ra Lee, Daegu (KR); Seung Joon Paik, Seoul (KR); Myoung Jun Jeong, Seoul (KR); Hyun Min Choi, Anyang-si (KR); Jung Min Lim, Anyang-si (KR)

(73) Assignee: Seoul National University Industry Foundation, Kwanak-Gu, Seoul (KR)

( * ) Notice: Subject to any disclaimer, the term of this patent is extended or adjusted under 35 U.S.C. 154(b) by 1532 days.

(21) Appl. No.: 11/284,384

(22) Filed: Nov. 21, 2005

(65) Prior Publication Data
US 2006/0241488 A1    Oct. 26, 2006

(30) Foreign Application Priority Data
Feb. 7, 2005    (KR) .................. 10-2005-0011477

(51) Int. Cl.
*A61B 10/00*    (2006.01)
(52) U.S. Cl. ...................... 600/564; 600/567
(58) Field of Classification Search ............... 600/562, 600/564, 567, 569, 570, 572; 606/167, 170, 606/184
See application file for complete search history.

(56) References Cited

U.S. PATENT DOCUMENTS
2002/0123697 A1 * 9/2002 Ishizaka et al. .............. 600/572
2004/0260201 A1 * 12/2004 Mueller, Jr. ................. 600/569

FOREIGN PATENT DOCUMENTS
JP    H5-237121    9/1993
JP    2001-170059    6/2001
KR    2004-34175    4/2004

OTHER PUBLICATIONS

"A Disposable MEMS-Based Micro-Biopsy Catheter for the Minimally Invasive Tissue Sampling" Authored by Sunkil Park, Ahra Lee, et al (inventors of current application) as presented to the IEEE IRS/RS International Conference on Intelligent Robots and Systems Aug. 2-6, 2005.

* cited by examiner

*Primary Examiner* — Max Hindenburg
*Assistant Examiner* — Jonathan M Foreman
(74) *Attorney, Agent, or Firm* — Head, Johnson & Kachigian, P.C.

(57) ABSTRACT

Disclosed is a catheter used to pick a sample of a lesion cell tissue existing in the living body, and more particularly a catheter capable of freely coupling or separating a micro biopsy tool and picking a tissue required for an examination just by inserting and extracting the biopsy tool into and from a lesion region when picking the tissue. The catheter can pick a tissue required to diagnose and treat an examinee with a minimal invasion. Accordingly, it is possible to alleviate the examinee's pain and to prevent a perforation from occurring in the picked region when picking the tissue. In addition, according to the catheter of the invention, since the micro biopsy tool can be easily mounted and separated, the catheter can be semi-permanently used by continuously replacing the biopsy tool only.

8 Claims, 18 Drawing Sheets

CATHETER CAPABLE OF BEING EQUIPPED WITH MICRO BIOPSY TOOL

CROSS-REFERENCE TO RELATED APPLICATION

The present application is claiming priority of Korean Patent Application No. 10-2005-0011477, filed on Feb. 7, 2005, the content of which is herein incorporated by reference.

BACKGROUND OF THE INVENTION

1. Field of the Invention

The present invention relates to a catheter used to pick a sample of a lesion cell tissue existing in a living body, and more particularly to a catheter capable of freely coupling or separating a micro biopsy tool and picking a tissue required for an examination just by inserting and extracting the biopsy tool into and from a lesion region when picking the tissue.

2. Background of the Related Art

A micro biopsy tool is a term referring to a needle or spike type micro tool capable of picking a micro tissue so as to examine and treat a lesion cell tissue existing in a living body. As an example of the micro biopsy tool, there is a barb-wired micro needle made of single crystal silicon. The micro biopsy tool can be manufactured through a micro-electro-mechanical system (MEMS) process, a LIGA (Lithographic, Galvanoformung, Abformung) process, a precision metal processing and a mold.

As a use example of the micro biopsy tool, a pathological examination picking a tissue sample from a patient so as to diagnose the patient's disease is a very important process to diagnose the disease and to determine a treatment method. The micro biopsy tools may be used with being mounted in a catheter which is a kind of conduit which is inserted into a human organ such as a blood vessel or an urethra.

However, since a diagnosis method using a catheter according to the prior art picks an examinee's cell tissue in great quantity beyond necessity due to its structural cause, thereby causing a pain and a risk to the examinee. In addition, as a typical picking method, there is a method of picking the tissue with forceps. However, according to this method, a great pain is caused to the examinee. Further, when an operator, who lacks an experience in the tissue picking, performs the medical treatment, a digestive organ such as the stomach is perforated, so that an emergency may occur.

For solving the above problems, there are suggested catheter tools made by applying a precise micro machining process. As an example, there is suggested a catheter having improved a shape of the forceps so as to increase an accuracy of the tissue picking and a picking amount. FIG. 1 shows a catheter used to pick a tissue sample according to the prior art. As shown, the catheter comprises forceps jaws 202, a micro needle 204 and a main body 201.

The catheter 200 shown in FIG. 1 has a structure such that the micro needle 204 having a concavo-convex structure is mounted to a center of the catheter and the forceps jaws 202 are mounted to both sides of the needle. The catheter 200 of FIG. 1 picks a tissue such a manner that a surface of the tissue is stretched when pricking and drawing the tissue 300 with the micro needle 204 and then the forceps jaws 202 pick up and separate the stretched tissue. The catheter 200 of FIG. 1 has an advantage of securing an accurate picking amount when picking the tissue.

However, when picking the tissue with the catheter 200 of FIG. 1, since two processes of pricking the tissue with the micro needle 204 and picking and separating the tissue with the forceps jaws 202 should be performed, an examinee's pain is increased. In addition, there is an inconvenience that a movement of forceps jaws 202 should be manipulated to separate the tissue under state that the tissue is stretched with the micro needle 204.

Additionally, since a catheter such that shown in FIG. 1 is manufactured to be integral with the forceps, it should be discarded after being used once for the tissue picking. In other words, the prior catheter can be used only for a disposable.

Accordingly, there is a need of a catheter capable of alleviating an examinee's pain and being easily manipulated and repeatedly used.

SUMMARY OF THE INVENTION

Accordingly, the present invention has been made to solve the above-mentioned problems occurring in the prior art. The object of the present invention is to provide a catheter equipped with a micro biopsy tool capable of picking a tissue with one invasion, thereby minimizing an examinee's pain due to the tissue picking.

Another object of the invention is to easily mount and separate a micro biopsy tool and thus to provide a catheter capable of being reused for another medical treatment by replacing only the micro biopsy tool after a medical treatment.

Still another object of the invention is to provide a catheter with which even an operator who lacks an experience in the tissue picking can easily pick the tissue just by picking the tissue with one invasion.

In order to accomplish the objects, there is provided a catheter comprising a fixing body capable of mounting a micro biopsy tool; and an external cover having the fixing body therein. The fixing body can be reciprocally moved in the external cover by a regulating wire passing through the external cover from an exterior. The external cover is formed with a front opening at a front surface thereof so that the micro biopsy tool can be reciprocally moved though the front opening, and a rear opening penetrated by the regulating wire at a rear surface.

As methods for mounting the micro biopsy tool to the fixing body, a method using a curve feature of a spring plate, a fixing method by two semicircular columns combined each other by a pin and formed with a recess respectively, a fixing method by a circular column formed with a recess and using adhesives or ultrasonic welding, and the like.

Additionally, the external cover may be constructed as a separate type which comprise an upper cover formed with a front opening at a front surface thereof so that the micro biopsy tool can be reciprocally moved when picking a tissue; and a lower cover detachably coupled to the upper cover and formed with a rear opening penetrated by the regulating wire at a rear surface. Or the external cover may be constructed as one body type which has specific shape of recess so as to restrict the fixing body not to rotate in the external cover and to regulate the length of the movement of the fixing body in the front and the rear.

In addition, the catheter according to the invention may be characterized in that the fixing body does not move laterally on the path of a tissue picking.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

Figure 1:
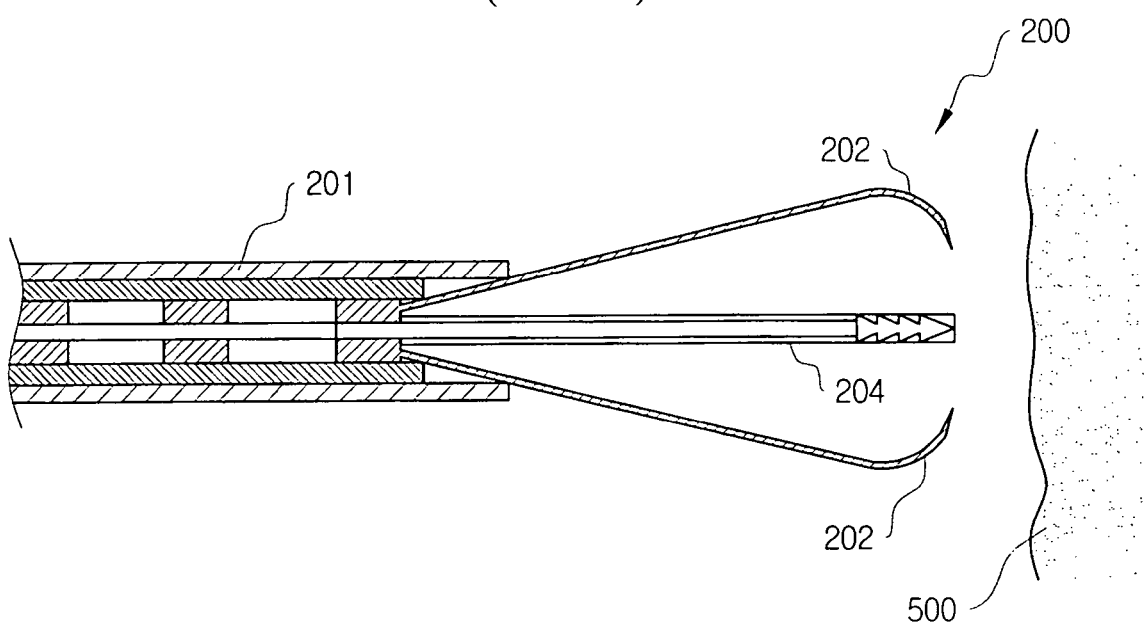
FIG. 1 shows a catheter used to pick a tissue sample according to the prior art.
Figure 2A:
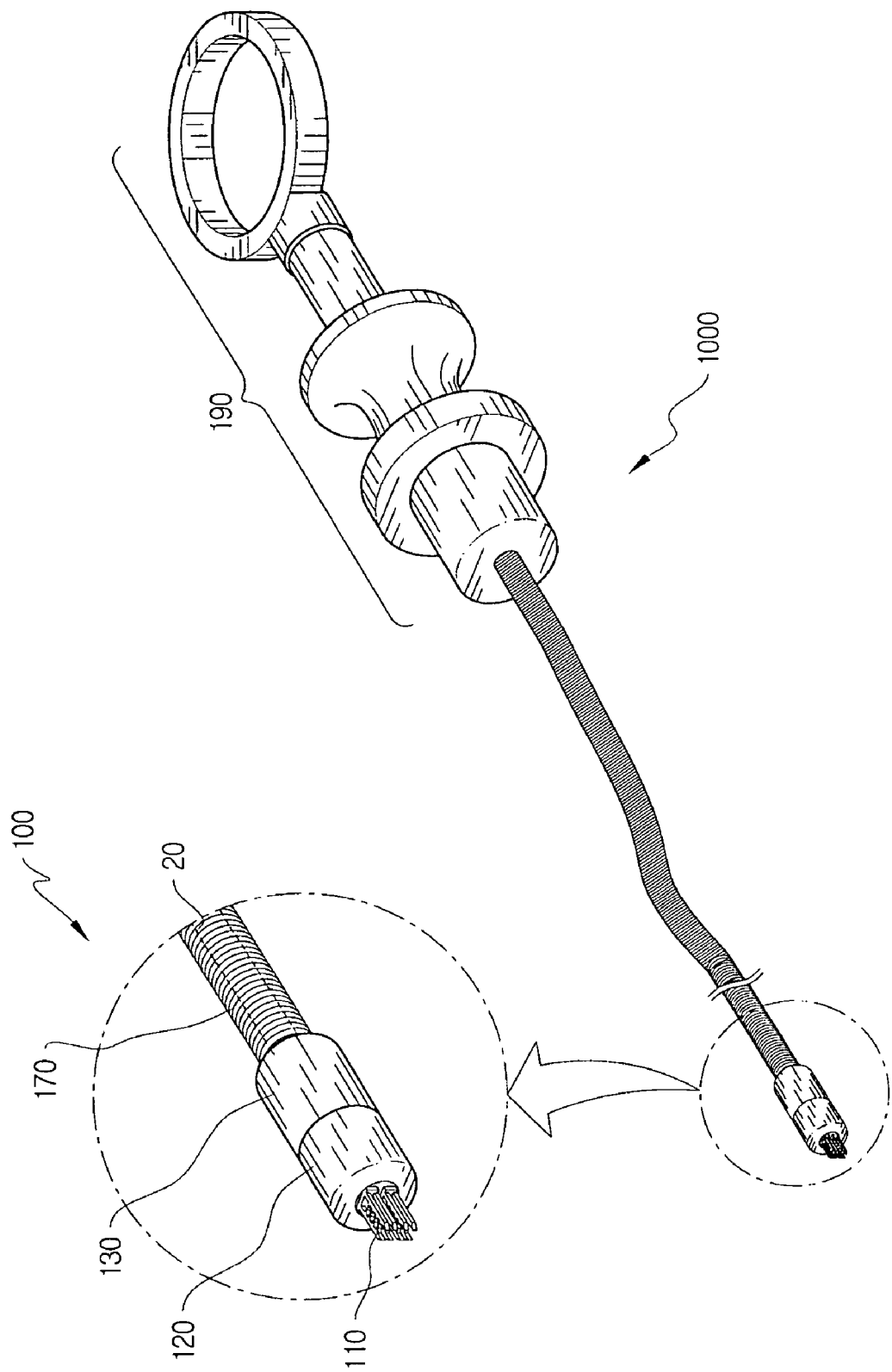
FIG. 2A shows a device for picking tissue including a catheter according to an embodiment of the invention.
Figure 2B:
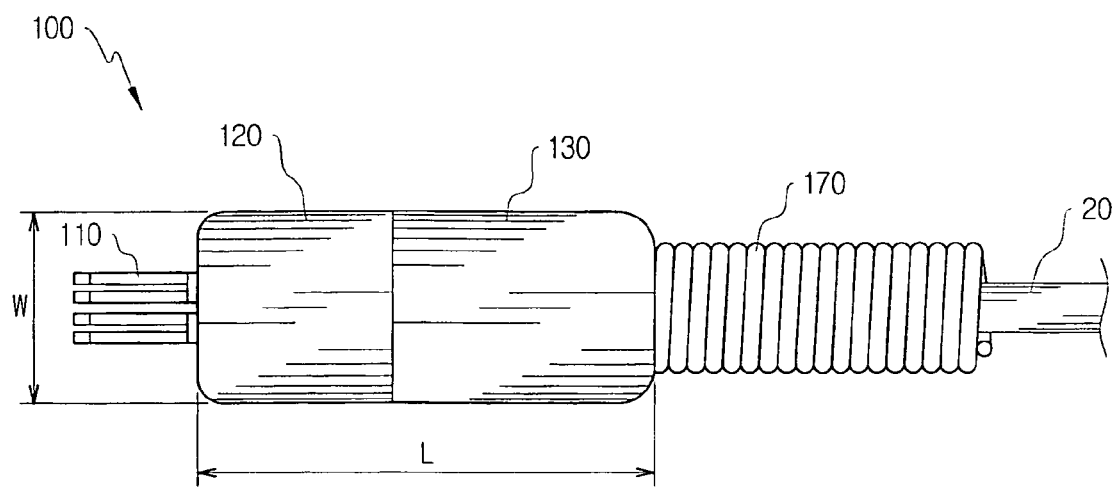
FIG. 2B shows an external structure of a catheter according to an embodiment of the invention.

FIGS. 2A and 2B show an external structure of a catheter 100 according to an embodiment of the invention and a device for picking tissue including the catheter 100. The catheter 100 shown in FIGS. 2A and 2B is equipped with a biopsy tool 110 and a body part of the catheter is mounted in external covers 120, 130. A regulating wire 20, which is capable of regulating a reciprocating motion of the biopsy tool 110 when picking a tissue, is extended to a regulating part 190 through the external cover. The regulating part 190 is structured to regulate the reciprocating motion of the regulating wire 20 automatically or manually.

Figure 3:
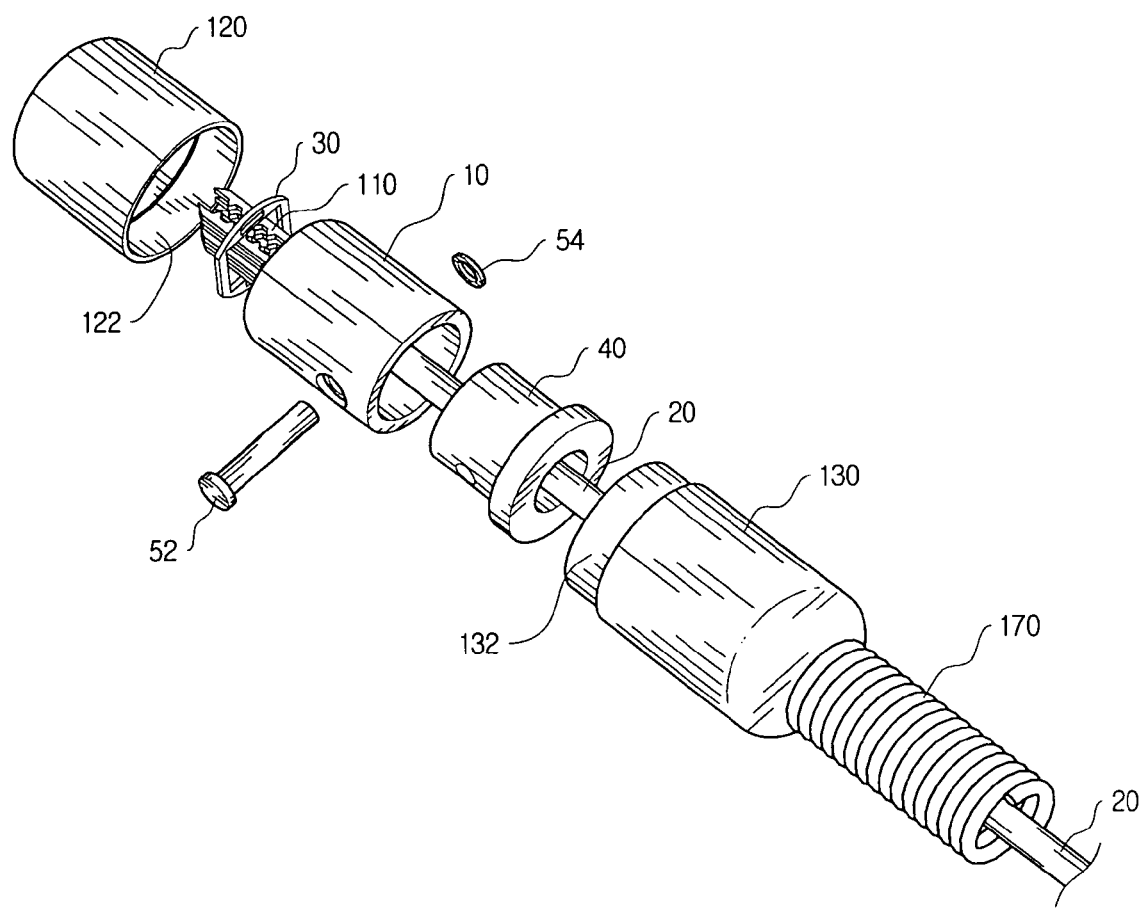
FIG. 3 is an exploded view of a catheter according to an embodiment of the invention.
Figure 4:
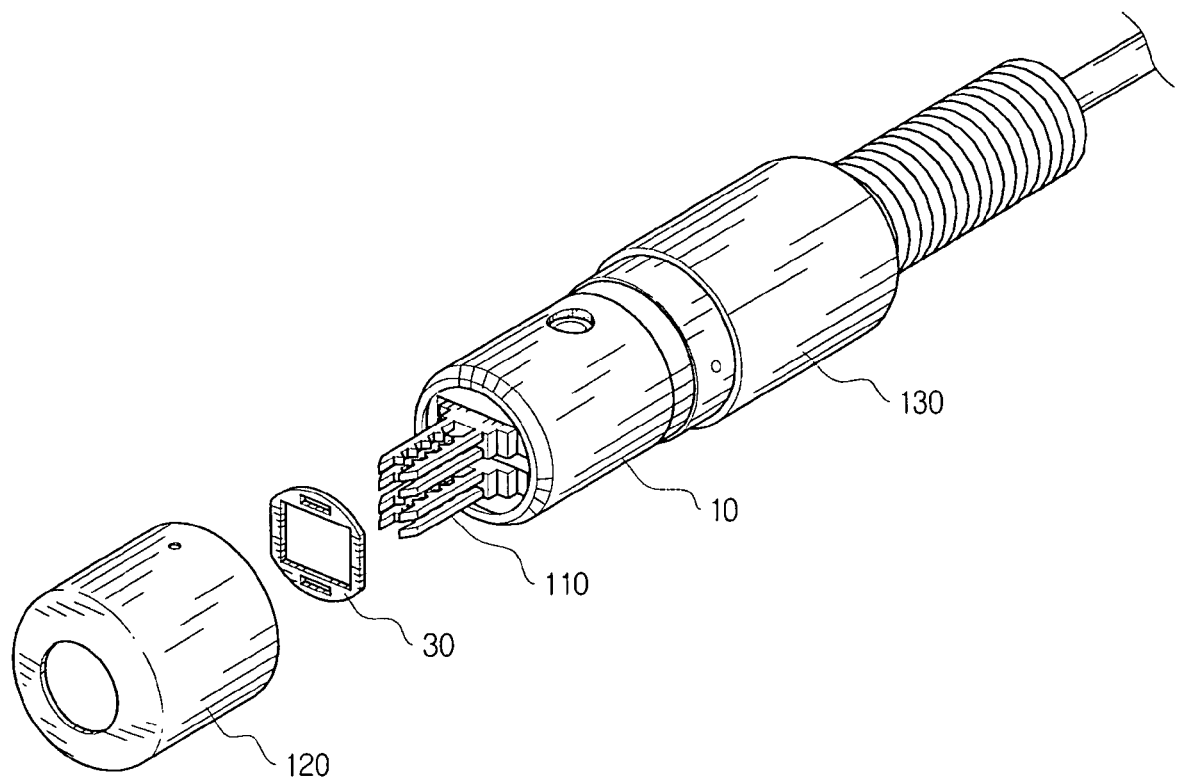
FIG. 4 is an exploded view of the catheter, viewing from a point other than in FIG. 3.

FIG. 3 is an exploded view of the catheter shown in FIGS. 2A and 2B. As shown, the body part of the catheter comprises a fixing body 10, the regulating wire 20 and a fixing plate 30. The external cover comprises an upper cover 120 and a lower cover 130.

The fixing body 10 is formed with a recess for inserting the biopsy tool 110 and directly coupled to the regulating wire 20. In the embodiment shown in FIG. 3, a fixing pin 52 is used to couple the fixing body 10 and the regulating wire 20. Like this, since the fixing body 10 is fixedly coupled to the regulating wire 20, the fixing body 10 is reciprocally moved when the Regulating wire 20 is reciprocally moved for picking a tissue.

Preferably, a wire guide 40 for restricting a lateral movement of the regulating wire 20 may be fixedly coupled to the fixing body 10 and the regulating wire 20. In this case, the fixing body 10, the regulating wire 20 and the wire guide 40 may be fixed with one fixing pin 52. The wire guide 40 can prevent the regulating wire 20 from being bended or collided with an inner wall of the external cover 120, 130 by restricting the lateral movement of the regulating wire 20, thereby causing the regulating wire 20 to reciprocally move smoothly in the external cover 120, 130.

The fixing plate 30 is provided to prevent the micro biopsy tool 110 from being separated from the fixing body 10 when the micro biopsy tool 110 is inserted into the fixing body 10. The fixing plate 30 is coupled to the fixing body 10 while covering a part of a surface of the micro biopsy tool 110. A detailed description of the fixing plate will be mentioned later.

A front surface of the upper cover 120 is formed with an opening so that the micro biopsy tool 110 can be reciprocally moved. That is, the micro biopsy tool 110 is mounted in the external cover and then protruded outwardly from the external cover by a regulation of the regulating wire 20 and then inserted into a tissue when picking the tissue. Like this, the front surface of the upper cover 120 is formed with the opening so that the micro biopsy tool 110 can be reciprocally moved in and out of the external cover.

The lower cover 130 is combined with the upper cover 120 to constitute the external cover. The upper and lower covers 120, 130 are formed with an annulus recess 122 and an annulus protrusion 132 having a concavo-convex shape at each of coupling portions thereof to easily separate or couple them, as shown in FIG. 3. The other side of the lower cover 130 is penetrated by the regulating wire 20.

Preferably, a protective pipe 170 for protecting an outwardly extended part of the regulating wire 20 and allowing a general reciprocating motion of the regulating wire 20 to be smoothly achieved may be bonded to the lower cover 130. The protective pipe 170 may be structured to extend from the lower cover 130 to the regulating part, thereby shielding and protecting the regulating wire 20. Preferably, the bonding of the lower cover 130 and the protective pipe 170 may be achieved with laser welding.

A size of the catheter is preferably limited within a predetermined range, considering a characteristic of the tool being inserted into a living body. From this point of view, in FIG. 2B, it is preferred that a length L of the external cover is within a range of 5 mm~15 mm, and a width W of the external cover is within a range of 1.0 mm~10 mm.

In addition, it can be structured that the external cover is formed into a cylindrical shape and has a round-shaped edge so as to smoothly move in the living body.

Figure 5:
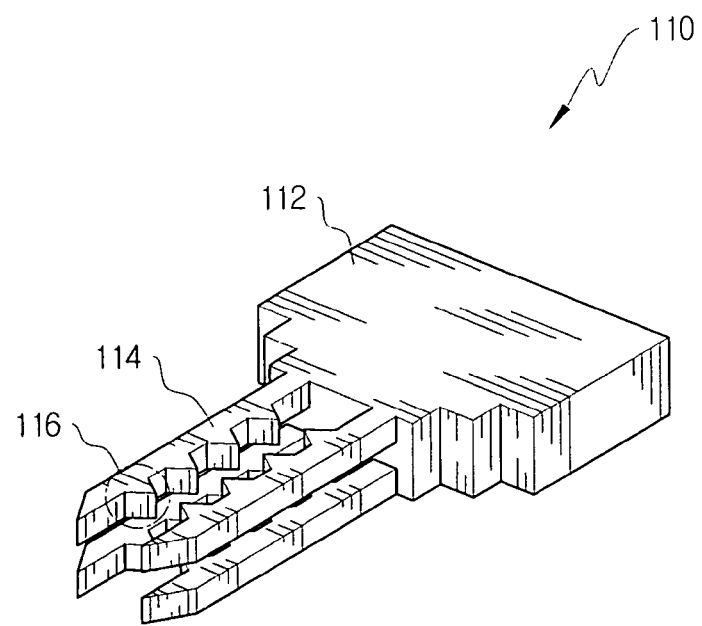
FIG. 5 illustrates an example of a biopsy tool equipped to a catheter according to an embodiment of the invention.

Hereinafter, each of elements constituting the body part will be more specifically described. FIG. 5 shows an example of the biopsy tool 110 equipped to the catheter of the invention. As shown, the biopsy tool 110 equipped to the catheter of the invention may comprise a body insertion part 112, an extension part 114 and a protrusion part 116. The body insertion part 112 is a part which is inserted into the recess formed in the fixing body 10 so as to couple to the fixing body 10. The extension part 114 is a part which is inserted into a tissue cell according to a regulation of the regulating part 190 when picking a tissue. The protrusion part 116 is a part which is protruded from a side surface of the extension part 112 and allows a tissue sample to be caught by the protrusion part and taken off together with it when the extension part is inserted and then extracted into and from the tissue cell.

Like this, since the biopsy tool 110 used in the embodiment of the invention can pick a tissue sample just by inserting and extracting the biopsy tool into and from a lesion region. A biopsy tool combined to a catheter according to the invention may be manufactured with three-dimensional structure having single crystal silicon as its raw material, or with two-dimensional structure through a precision metal processing and LIGA (Lithographic, Galvanoformung, Abformung) process.

Figure 6:
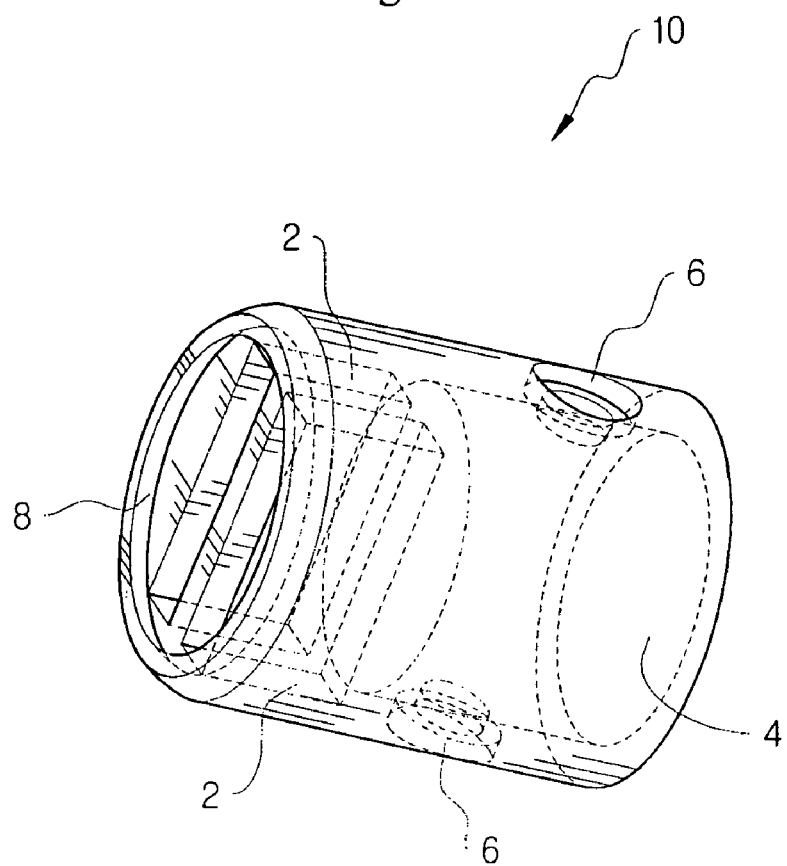
FIG. 6 shows a fixing body constituting a catheter according to an embodiment of the invention.

FIG. 6 shows the fixing body 10 constituting the body part of the catheter of the invention. As shown, the fixing body 10 is formed with recesses 2 for inserting and fixing the biopsy tool 110 and a space 4 for coupling to the wire guide 40 and the regulating wire 20. In addition, it is formed with an aperture 6 for inserting the fixing pin 52 when the fixing body is coupled with wire guide 40 and the regulating wire 20 using the fixing pin 52. Like this, the fixing body 10 is fixedly coupled with the regulating wire 20 and thus reciprocally moves together with the regulating wire 20 in the external cover 120, 130 when picking the tissue.

Although the fixing body is formed with the two recesses 2 for inserting the biopsy tool 110, one or more recesses may be formed as necessary. After inserting the biopsy tool 110 into the recesses, the fixing plate 30 is coupled with the fixing body 10 so as to prevent the tool from being arbitrarily separated. The fixing body 10 is formed with a recess 8 for coupling to the fixing plate 30 at an inner circumference of an inlet thereof.

Figure 7A:
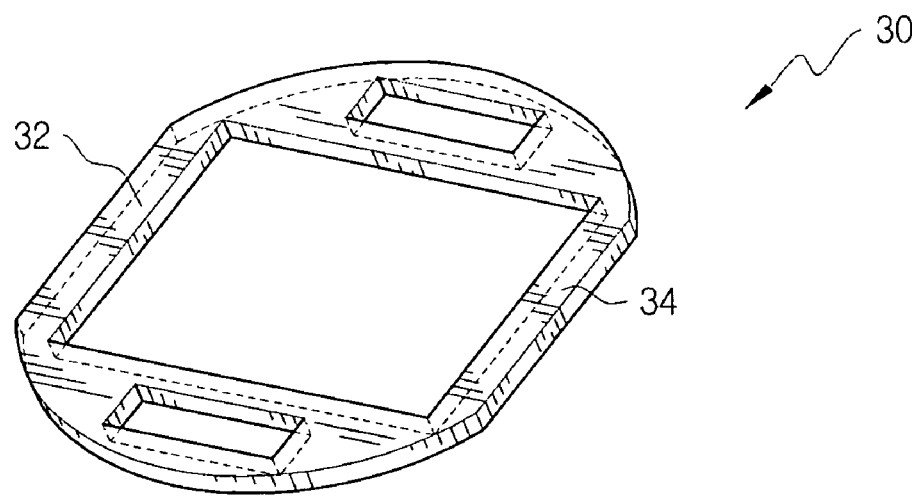
FIG. 7A shows a fixing plate constituting a catheter according to an embodiment of the invention.
Figure 7B:
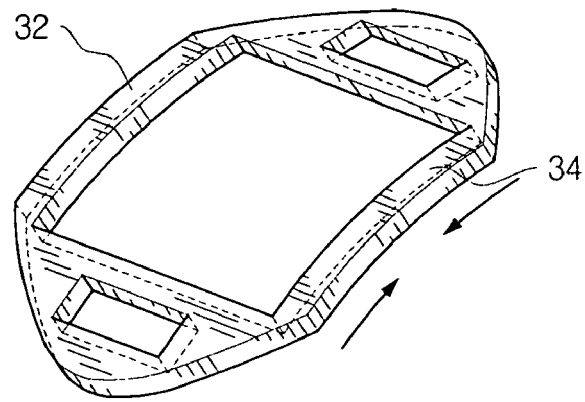
FIG. 7B shows that the fixing plate shown in FIG. 7A is bended.

FIGS. 7A and 7B show the fixing plate 30 coupling to the fixing body 10 so as to prevent a separation of the biopsy tool 110. As shown in FIG. 7B, the fixing plate 30 is made of an elastic material enough to bend and fit it into the fixing recess 8 of the fixing body from an exterior. In other words, in order to fit the fixing plate 30 into the recess 8 of the fixing body 10, a force is applied to the fixing plate 30 to bend under state that the fixing plate 30 is picked up with a hand or pincettes. Then, under the bended state, the fixing plate is inserted into an inlet of the fixing body 10 and fitted into the recess 8 formed in the inner surface thereof. Like this, when the fixing plate 30 is coupled with the fixing body 10, each side parts 32, 34 of the fixing plate cover a part of a surface of the biopsy tool 110 inserted into the fixing body, so that it is possible to prevent the biopsy tool 110 from being arbitrarily separated.

Figure 8A:
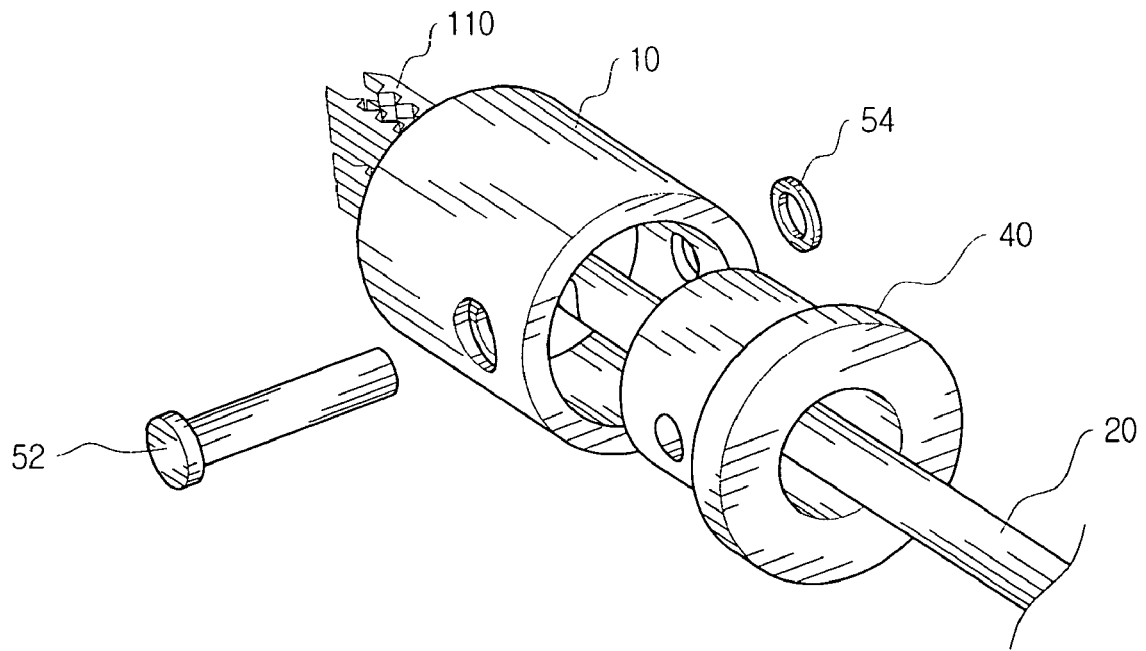
FIG. 8A shows a shape that each constituent of a catheter according to an embodiment of the invention is disassembled.
Figure 8B:
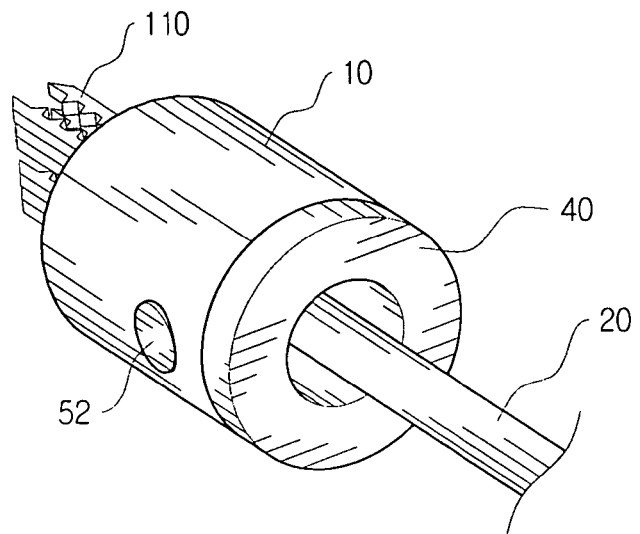
FIG. 8B shows that each constituent of the catheter shown in FIG. 8A is assembled.

FIGS. 8A and 8B show a coupled state of the fixing body 10, the regulating wire 20 and the wire guide 40 of the catheter of the invention. As shown, each of the fixing body 10, the regulating wire 20 and the wire guide 40 is formed with an aperture for passing the fixing pin 52, so that they can be fixedly coupled using one fixing pin 52. The fixing body 10, the regulating wire 20 and the wire guide 40 coupled like this reciprocally moves together in the external cover when picking the tissue. After inserting the fixing pin 52, a pad 54 can be coupled with a lower end of the fixing pin 52 outwardly protruding from the aperture, so as to prevent the fixing pin from being separated.

Figure 9A:
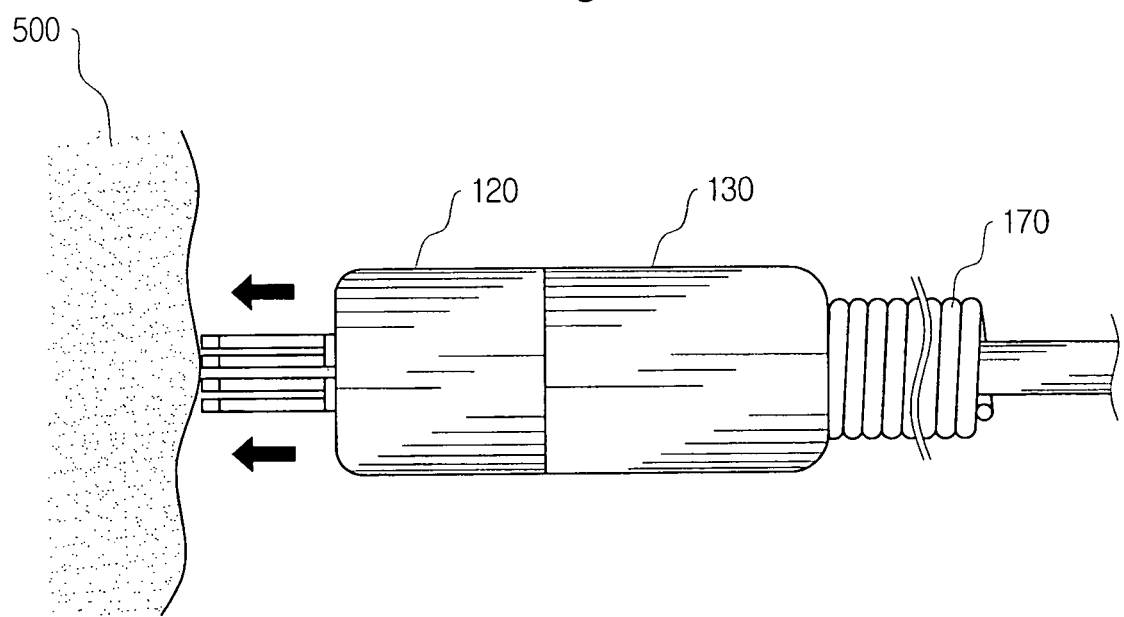
FIG. 9A shows that a catheter according to an embodiment of the invention is inserted to tissues in order to pick a tissue sample.
Figure 9B:
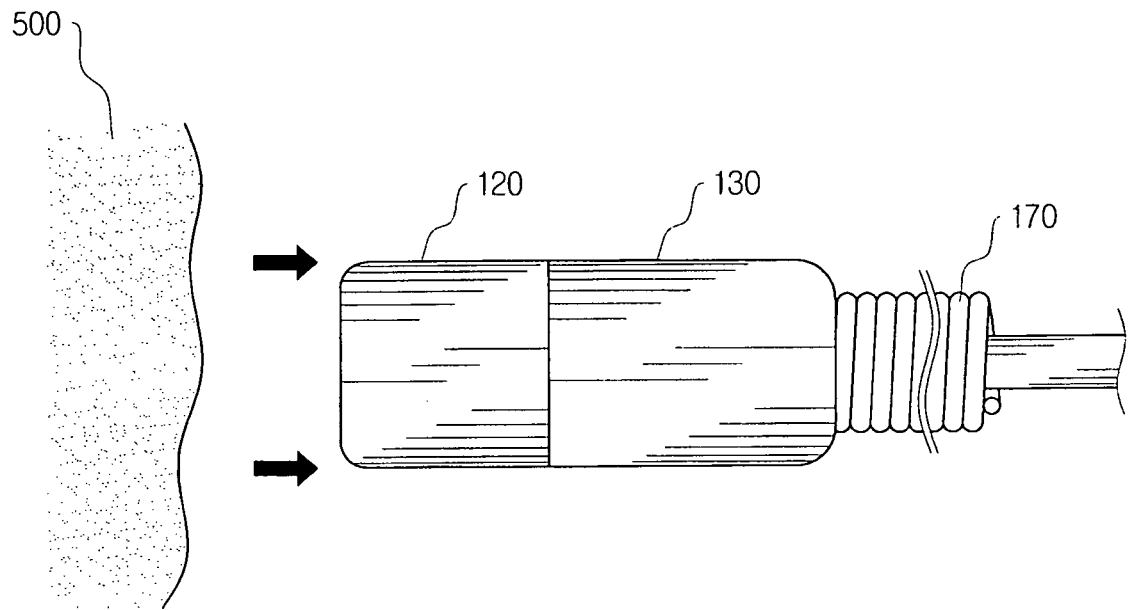
FIG. 9B shows that the catheter of FIG. 9A is drawn from the tissues.

FIGS. 9A and 9B show a process of picking the tissue sample with the catheter of the invention. As shown in FIG. 9A, the extension part 114 (referring to FIG. 5) of the biopsy tool 110 is inserted into the tissue 500 so as to pick the tissue sample. Under state that the extension part of the biopsy tool 110 is inserted, the regulating wire 20 is manipulated through a regulating part 190 (referring to FIG. 2A) in the exterior of the living body, thereby causing the biopsy tool 110 inserted into the tissue 500 to be extracted and to get into the external cover 120, 130. FIG. 9B shows a state that the extension part 114 of the biopsy tool has gotten into the external cover. That is, the extension part 114 of the biopsy tool 110 is extracted from the tissue 500 and allowed to get into the external cover 120, 130 by rearward moving the body part of the catheter combining with the regulating wire 20 of the regulating part 190. In this case, during the extraction of the biopsy tool 110, the tissue sample is caught between the extension part 114 of the biopsy tool 110 and taken off together with it, and the tissue sample taken off gets into the external cover 120, 130 together with the extension part 114. Like this, since the tissue sample moves to the exterior of the living body under state that it is embedded in the external cover, it is possible to safely move the tissue sample without losing it.

Figure 10A:
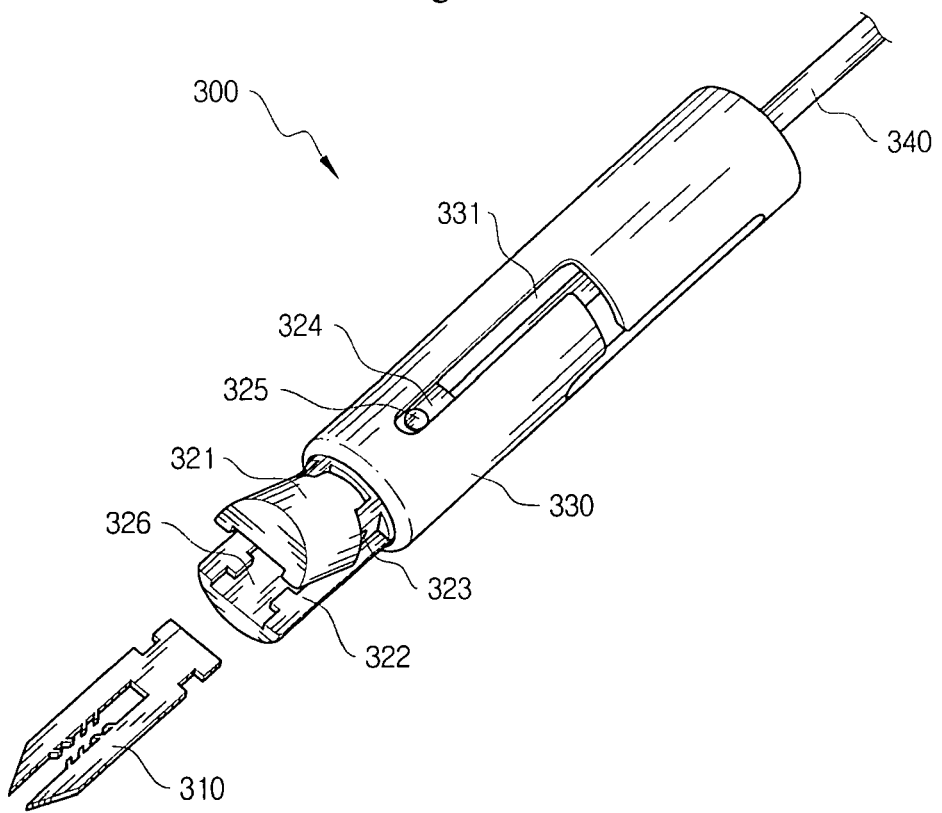
FIG. 10A shows a catheter according to another embodiment of the invention.

A catheter according to another embodiment of the invention is shown in FIG. 10A. For the catheter 300 of FIG. 10A, a fixing body 324 having a convex and circular protrusion 325 moves in an external cover 330 having a cylinder shape formed with a recess 331 of specific path. Like this, it is possible to guide the movement of the fixing body 324 and restrict the lateral movement and round movement, which is not intended, of the fixing body 324 in the external cover 330. In addition, the movement length in the front-rear direction may be regulated in accordance with the length of the recess 331.

Meanwhile, as shown in FIG. 10A, the fixing body 324 may be manufactured such that a corresponding portion combining with a micro biopsy tool 310 is divided into a cover part 321 and a base part 322, wherein the cover part 321 and the base part 322 may be combined by a pin 323 so that a separation and a combination of the micro biopsy tool 310 can be performed easily. A specific description for the fixing body 324 will be described later.

Figure 10B:
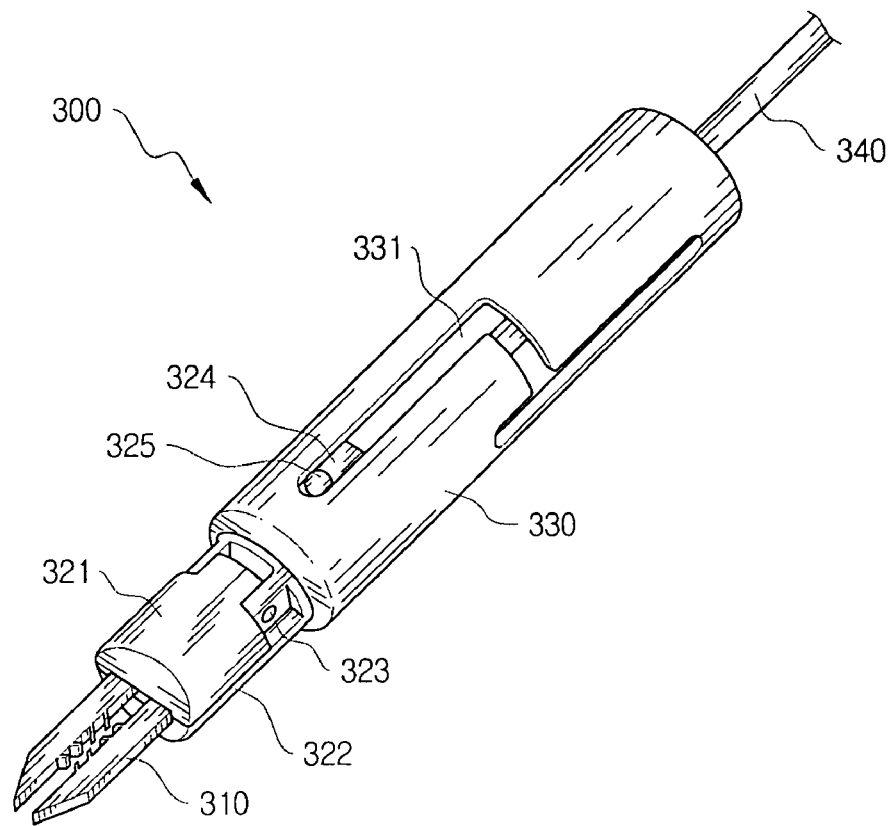
FIG. 10B shows the catheter of FIG. 10A mounting a micro biopsy tool.
Figure 10C:
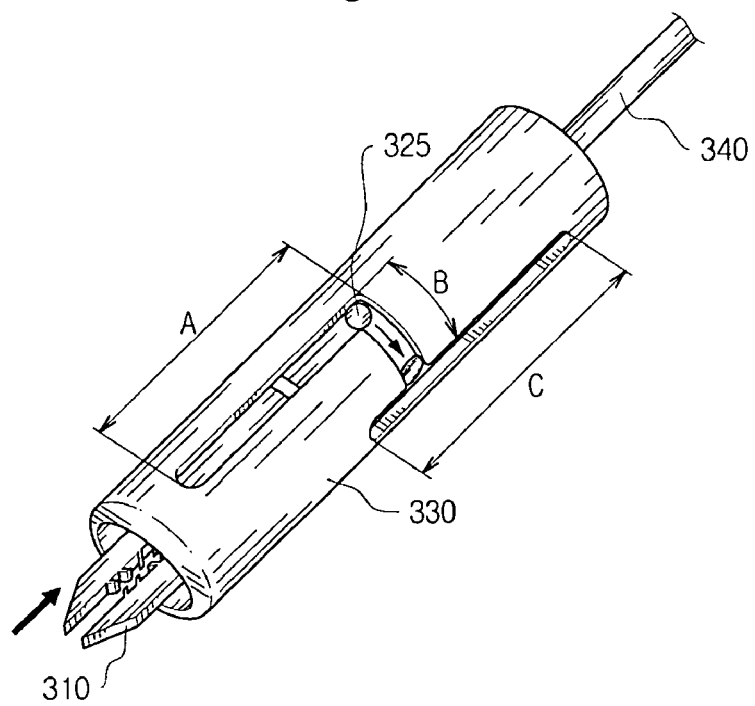
FIG. 10C shows that a fixing body mounting the micro biopsy tool moves along a recess of an external cover in FIG. 10A.

As described in the above, the operation of the catheter 300 can be controlled by the regulating wire 340. FIGS. 10B, 10C, 10D and 10E show the operation process of the catheter 300. FIG. 10B shows the catheter mounting a micro biopsy tool. In FIG. 10B, the protrusion 325 formed on the fixing body 324 is in a state to moving to the front end of the path of the recess 331. As shown in FIGS. 10A and 10B, for the fixing body 324, the micro biopsy tool 310 can be simply mounted by putting the micro biopsy tool 310 in the portion of which cover part 321 is in open state, and then closing the cover part 321. FIG. 10C shows that the fixing body 324 mounting the micro biopsy tool 310 moves in the rear direction along the recess 331 of the cover 330. As shown in FIG. 10C, the fixing body 324 moved along the 'A' path of the path formed to the external cover 330, and then moves along the 'B' path.

Figure 10D:
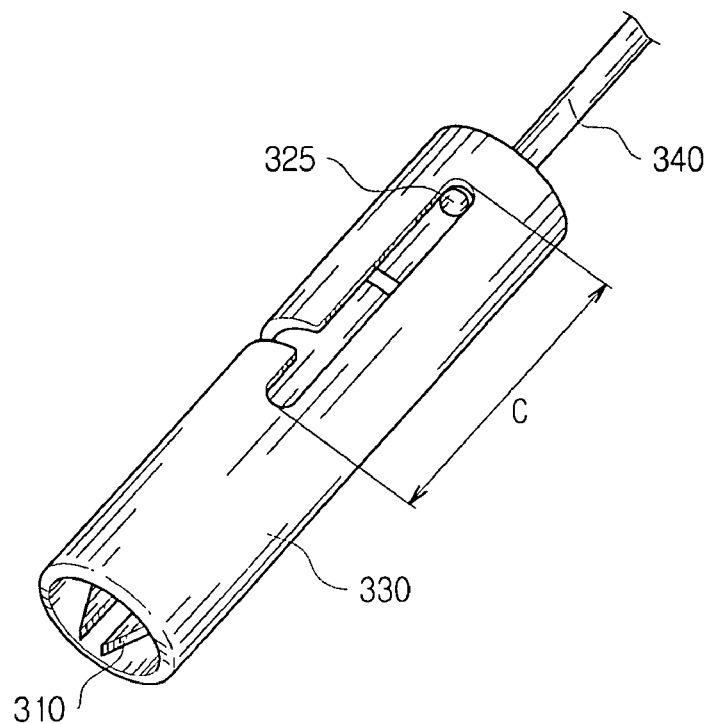
FIG. 10D shows that the fixing body mounting the micro biopsy tool has moved to a standby state for picking a tissue in FIG. 10A.

FIG. 10D shows that the fixing body 324 mounting the micro biopsy tool 310 is in a standby state for picking a tissue by moving to the rear end of the path of the recess 331. The fixing body 324 may be in the standby state by moving in the rear direction along the 'C' path after moving along the 'A' path and the 'B' path of the recess 331 sequentially as shown in FIG. 10C. The catheter 300 may be constructed such that the micro biopsy tool 310 does not protrude outside of the external cover 330 in the standby state for picking a tissue.

Figure 10E:
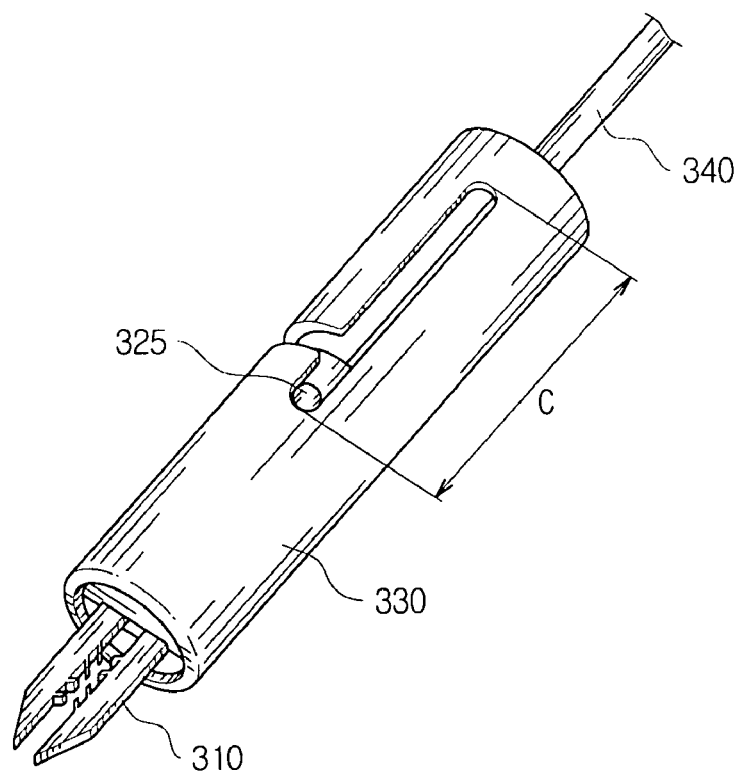
FIG. 10E shows that the fixing body mounting the micro biopsy tool has moved to a state for picking a tissue in FIG. 10A.

FIG. 10E shows that the fixing body 324 mounting the micro biopsy tool 310 has moved in a state for picking a tissue. As shown in FIG. 10E, the catheter 300 may be constructed such that the fixing body 324 does not protrude outside of the external cover 330, only while the micro biopsy tool 310 protrudes outside of the external cover 330 in the state for picking a tissue. Like this, in the state that the micro biopsy tool 310 protrudes outside of the external cover 330, the micro biopsy tool 310 is inserted into tissues(not shown) in order to pick a tissue sample. After that, as shown in FIG. 10E, it is possible to pick a tissue sample by moving the fixing body 324 in the rear direction along the 'C' path.

Figure 10F:
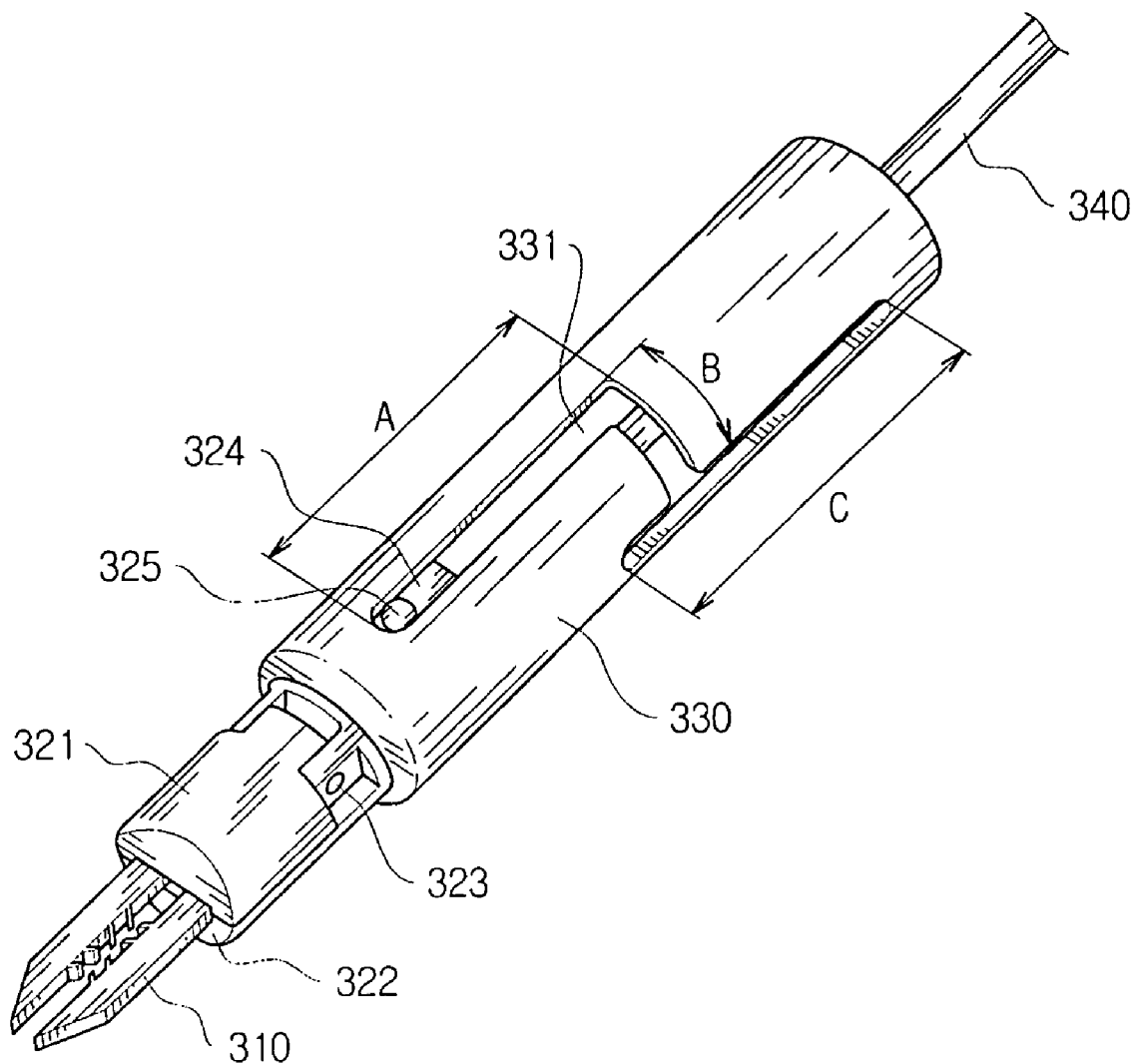
FIG. 10F shows that the fixing body has moved to a state that the micro biopsy tool can be separated from it in FIG. 10A.

FIG. 10F shows that the fixing body 324 has moved in state in which is capable of separating the micro biopsy tool 310 from it. After completing the picking of tissue, the protrusion 325 being on the 'C' path is moved in the front direction along the 'B' path and 'A' path sequentially, so that the cover part 321 of the fixing body 324 is to be protruded outside of the external cover 330. And then, the micro biopsy tool 310 can be separated from the fixing body 324 by opening the cover part 321.

Figure 11A:
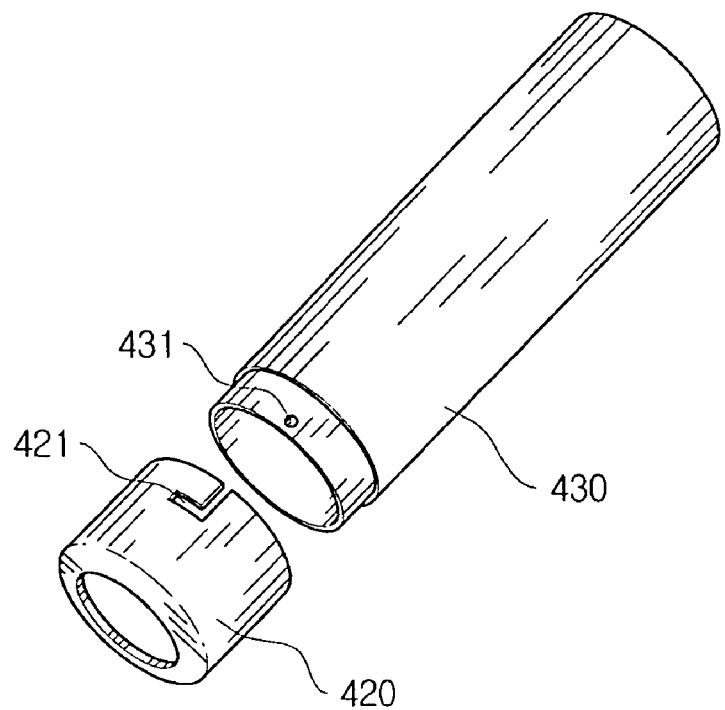
FIG. 11A shows an external cover according to another embodiment of the invention.
Figure 11B:
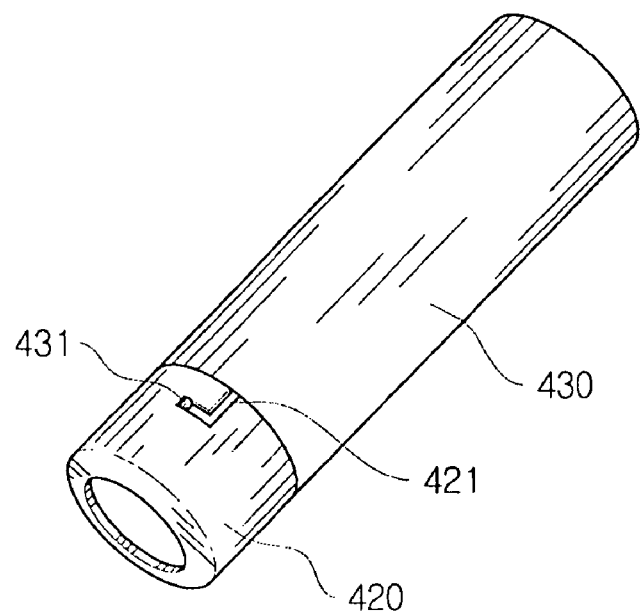
FIG. 11B shows a state that an upper cover and a lower cover constituting the external cover of FIG. 11A respectively are combined to each other.

External covers 420, 430 being a separate type according to another embodiment of the invention is shown in FIG. 11A. In FIG. 11A, the cover 420 of the external covers is formed with a recess 421 of " ⊓ " shape and the other cover 430 is formed with a protrusion 431 of circular shape, and thereby recess 421 and the protrusion 431 may form a concavo-convex structure to each other. Therefore, the two covers 420, 430 can preserve an stable combination state by the coupling of the recess 421 and the protrusion 431. FIG. 11B shows a combination state of the upper cover 420 and the lower cover 430.

Figure 12A:
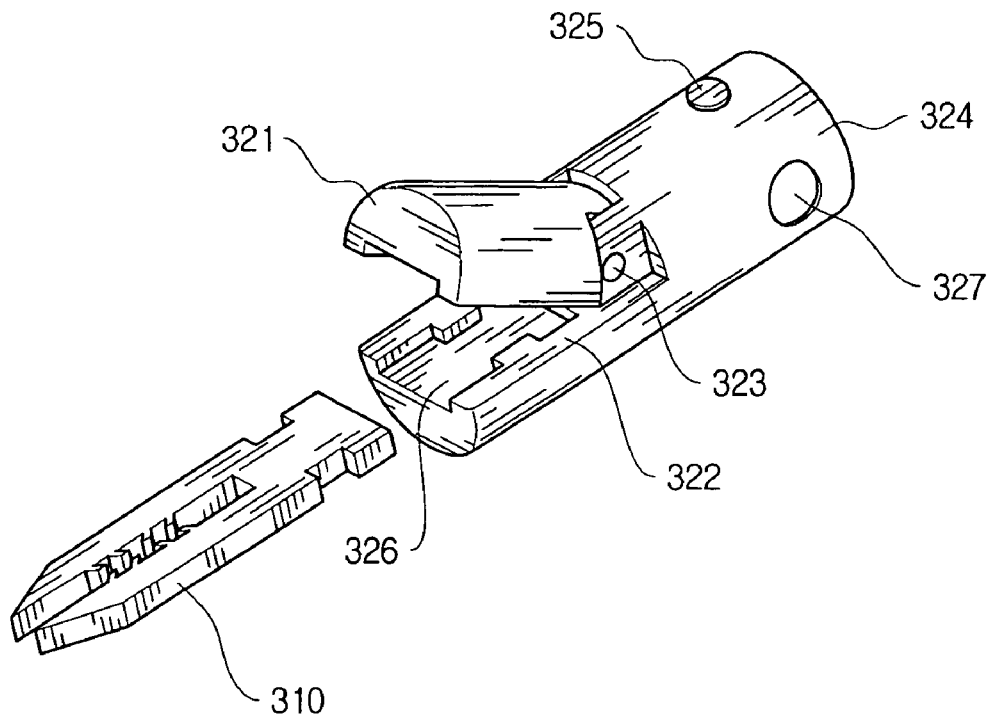
FIG. 12A shows a fixing body according to another embodiment of the invention.

FIG. 12A shows the fixing body 324 adopted in the catheter of FIG. 10A. As shown in FIG. 12A, a recess 326 is formed on a base part 322 of the fixing body 324 for putting a micro biopsy tool thereon, and another recess having identical shape with the recess 326 is also formed on a cover part 321. The cover part 321 may be combined with the base part 322 through a pin 323, so that the cover part 321 may rotate to the base part 322 within a prescribed angles, and thereby the micro biopsy tool 310 can be easily separated/combined. A hole 327 may be formed for combination with the regulating wire 340 (referring to FIG. 10A) through a pin. As described in the above, the protrusion 325 formed on the surface of the fixing body 324 moves along the path of the recess 331, and thereby enables the fixing body 324 to move stably in the external cover.

Figure 12B:
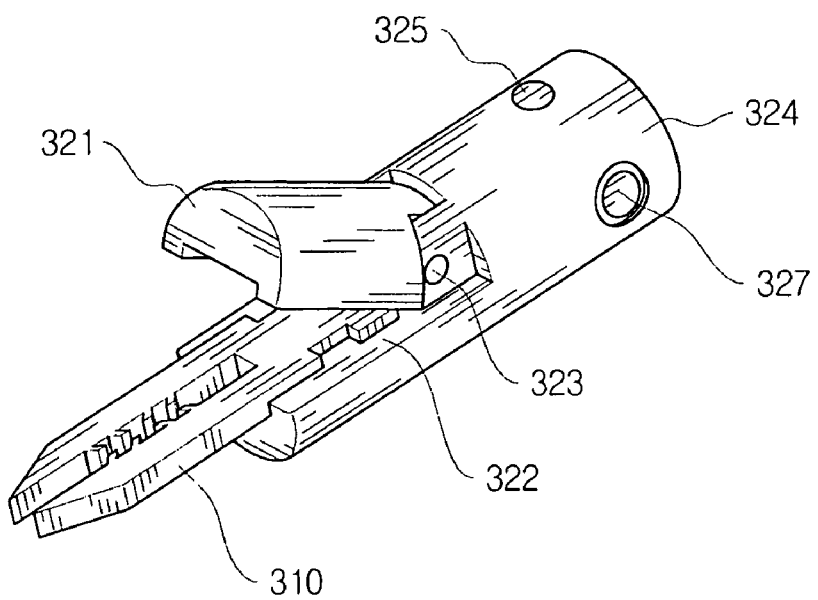
FIG. 12B shows that a micro biopsy tool is mounted to the fixing body of FIG. 12A.

FIG. 12B shows that a micro biopsy tool is mounted to the fixing body 324 of FIG. 12A. As shown in FIG. 12B, the micro biopsy tool 310 can be fixed to the fixing body 324 by closing the cover part 321 when the micro biopsy tool 310 is put on the base part 322 of the fixing body 324.

Figure 13A:
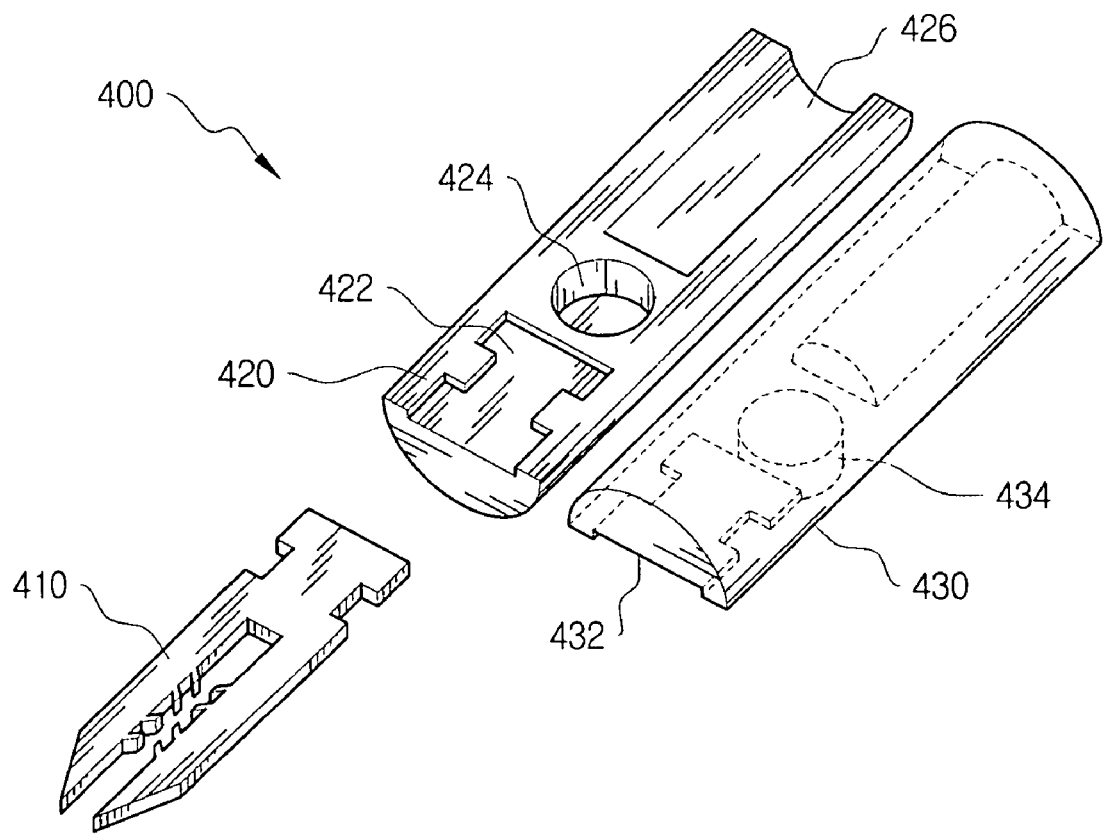
FIG. 13A shows a fixing body constituted by two semicircular columns according to another embodiment of the invention.

FIG. 13A shows a fixing body 400 according to another embodiment of the invention. For the fixing body 400 of FIG. 13A, a micro biopsy tool 410 may be fixed by being inserted between recesses 422, 432 formed on two semicircular columns 420, 430, respectively. Like this, while the recesses 422, 432 are formed on two semicircular columns 420, 430, respectively, a recess 424 is formed on surface of one column 420 and a protrusion 434 is formed on surface of another column 430, so that two semicircular columns 420, 430 have a stable combination to each other. Hereby, two semicircular columns 420, 430 may have a concavo-convex structure to each other. In FIG. 13A, the recess 426 formed on the rear part of the fixing body 420 is to mount a regulating wire.

Figure 13B:
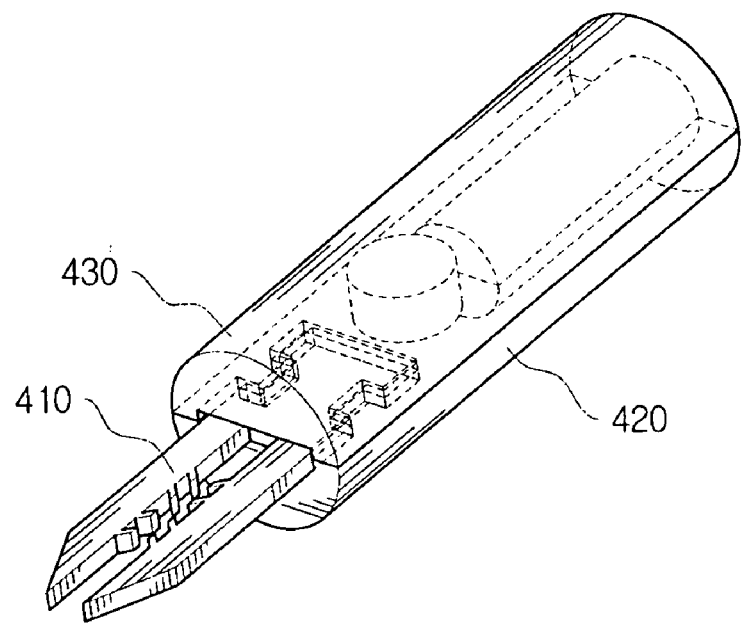
FIG. 13B shows that two semicircular columns shown in FIG. 13A are combined to each other.

FIG. 13B shows the fixing body 400 of FIG. 13A mounting the micro biopsy tool 410.

Figure 14A:
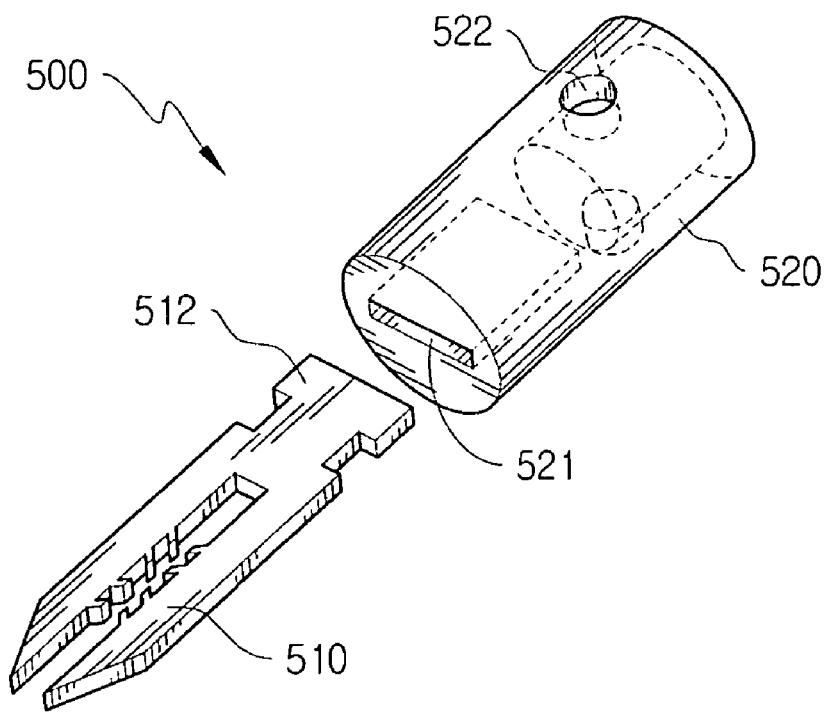
FIG. 14A shows a fixing body according to another embodiment of the invention.

FIG. 14A shows a fixing body 500 according to another embodiment of the invention. In the embodiment of FIG. 14A, the micro biopsy tool 510 is inserted into a recess of specific shape formed on front surface of the fixing body 500. In this case, the micro biopsy tool 510 may be stably fixed with the fixing body 500 by applying adhesives to a corresponding part 512 of the micro biopsy tool 510 or ultrasonic welding.

Figure 14B:
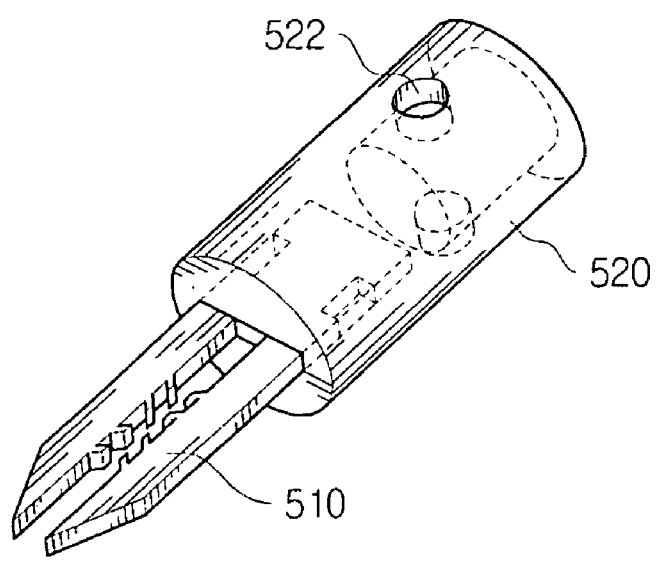
FIG. 14B shows that a micro biopsy tool is mounted to the fixing body of FIG. 14A.

FIG. 14B shows that the micro biopsy tool 510 is mounted to the fixing body 520 of FIG. 14A.

Figure 15A:
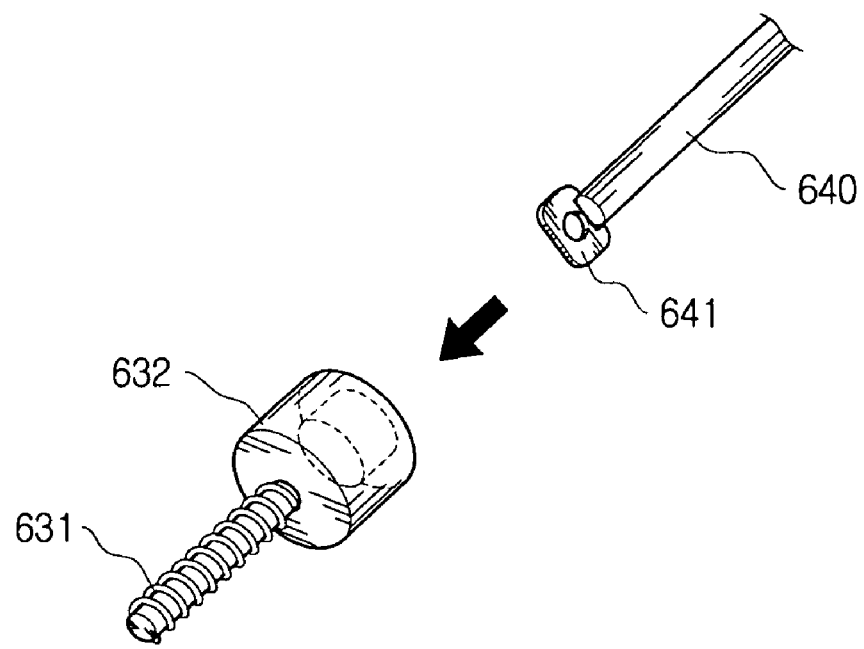
FIG. 15A shows a fixing body according to another embodiment of the invention.

FIG. 15A shows that the first fixing body 632 is combining with the combining part 641 of the regulating wire 640 according to another embodiment of the invention. In the embodiment of FIG. 15A, the first fixing body 632 may be combined with the regulating wire 640 by welding, and a bolt 631 for combining with the second fixing body 620 may be formed at an end of the first fixing body 632.

Figure 15B:
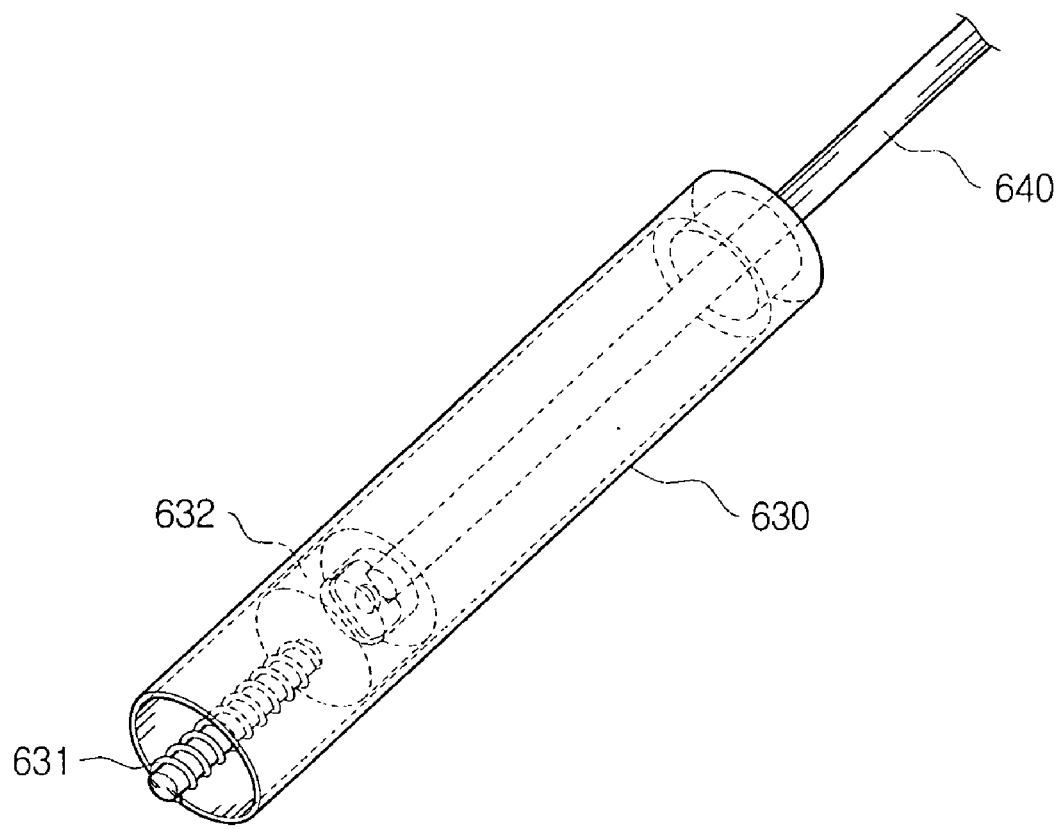
FIG. 15B shows that the fixing body of FIG. 15A is combined to a regulating wire.

FIG. 15B shows that the first fixing body 632 and the regulating wire 640 combined to each other according to the embodiment of FIG. 15A are contained in an external cover 630.

Figure 15C:
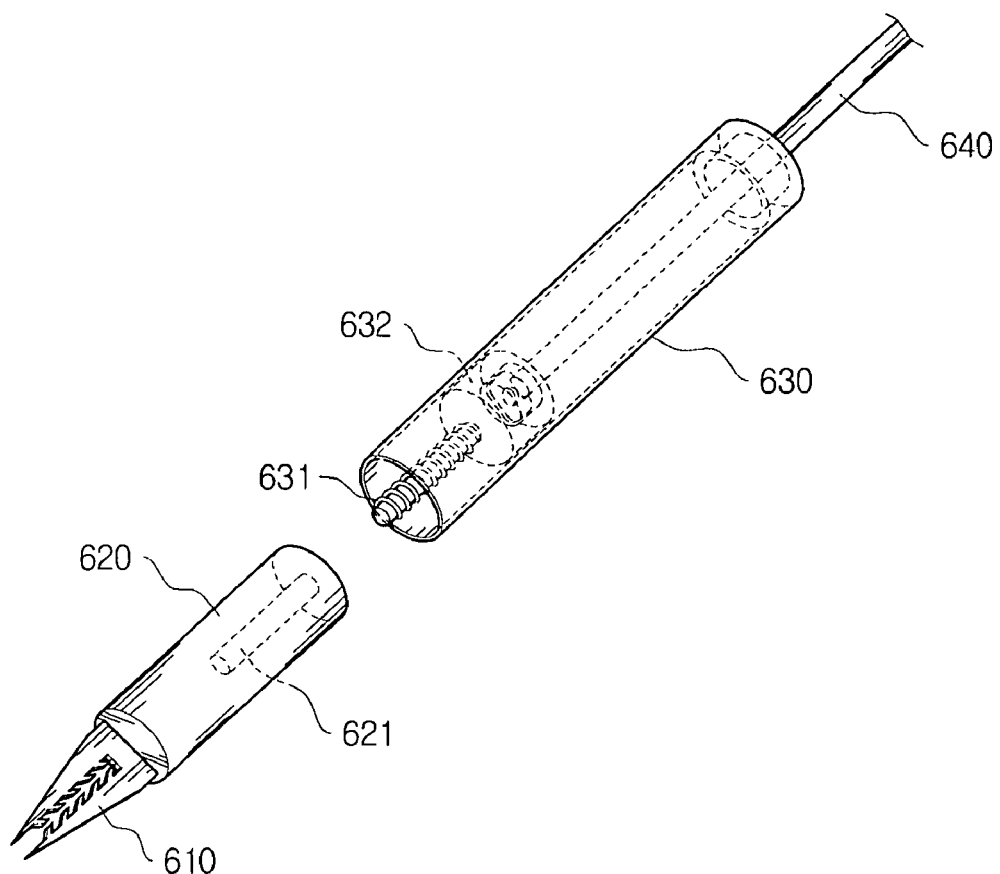
FIG. 15C shows that the fixing body of FIG. 15B is combining to a micro biopsy tool with a bolt.

FIG. 15C shows to combine the second fixing body 620, which mounts a micro biopsy tool, with the first fixing body 632 through the bolt 631 formed at an end of the first fixing body 632. As shown in FIG. 15C, a hole 621, which has screw line therein for combining with the bolt 631, may be formed in an inner part of the second fixing body 620.

Figure 15D:
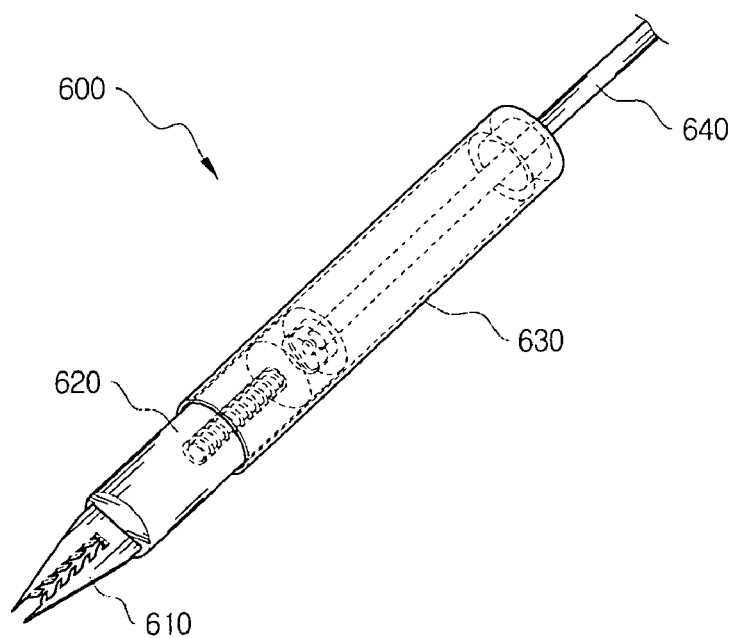
FIG. 15D shows that the fixing body of FIG. 15B has combined to a micro biopsy tool.

FIG. 15D shows a catheter 600 constructed by the combination of the first fixing body 632 and the second fixing body 620 according to the embodiment of FIG. 15C. In case using the catheter 600 of FIG. 15D, a tissue sample may be picked through simple manipulation to move the regulating wire 640 reciprocally, as the catheters according to other embodiments described in the above.

Like this, when using the catheter of the invention, it is possible to pick the tissue sample just by inserting and extracting the biopsy tool into and from the tissue cell. Accordingly, the picking process can be performed more easily than the picking method using the needle and forceps according to the prior art.

As described above, the catheter according to the invention picks the tissue with one invasion, thereby minimizing an examinee's pain due to the tissue picking.

In addition, since it is possible to easily mount and separate the micro biopsy tool, even after a medical treatment, the catheter can be reused for another medical treatment by replacing the micro biopsy tool only. Accordingly, the invention has a superior advantage from a point of view of an efficient use of resources.

Additionally, since the catheter can pick the tissue sample with only one invasion, such as just by inserting and extracting the biopsy tool into and from the tissue cell, even an operator who lacks an experience in the tissue picking can easily pick the tissue.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A catheter comprising;
   a fixing body capable of mounting a micro biopsy tool; and
   an external cover having the fixing body therein;
      wherein the fixing body can be reciprocally moved in the external cover by a regulating wire passing through the external cover from an exterior,
   the external cover is formed with a front opening at a front surface thereof so that the micro biopsy tool can be reciprocally moved through the front opening, and a rear opening penetrated by the regulating wire at a rear surface;
   the fixing body comprising a fixing plate coupled to the fixing body and disposed between the front surface of the external cover and a part of a surface of the micro biopsy tool; and
   the fixing plate covers the part of the surface of the micro biopsy tool so as to prevent the micro biopsy tool from being separated from the fixing body through the front opening of the external cover.

2. The catheter according to claim 1, wherein the fixing body comprises a wire guide fixedly coupled to the regulating wire to restrict a lateral movement of the regulating wire in the external cover.

3. The catheter according to claim 2, wherein the wire guide is fixedly coupled to the regulating wire and the fixing body with one fixing pin.

4. The catheter according to claim 1, wherein the fixing body is formed with a fixing recess at an inner circumference of an inlet thereof into which the fixing plate is inserted, and the fixing plate is made of an elastic material enough to fit it into the fixing recess from the exterior.

5. The catheter according to claim 1, wherein a length of the external cover is between 5 mm and 15 mm, and a width of the external cover is between 1.0 mm and 10 mm.

6. The catheter according to claim 1, wherein the external cover is formed into a cylindrical shape and has a round-shaped edge for a smooth insertion into a living body.

7. The catheter according to claim 1, wherein the external cover is bonded with a protective pipe which protects an outwardly extended part of the regulating wire and covers the regulating wire so as to allow a general reciprocating motion of the regulating wire to be smoothly achieved.

8. The apparatus for picking tissue cells comprising a catheter, the catheter comprising:
   a fixing body capable of mounting a micro biopsy tool; and
   an external cover having the fixing body therein,
      wherein the fixing body can be reciprocally moved in the external cover by a regulating wire passing through the external cover from an exterior;
   the external cover formed with a front opening at a front surface thereof so that the micro biopsy tool can be reciprocally moved through the front opening, and a rear opening penetrated by the regulating wire at a rear surface;
   the fixing body comprising a fixing plate coupled to the fixing body and disposed between the front surface of the external cover and a part of a surface of the micro biopsy tool; and
   the fixing plate covers the part of the surface of the micro biopsy tool so as to prevent the micro biopsy tool from being separated from the fixing body through the front opening of the external cover.

* * * * *